United States Patent [19]

Papa

[11] Patent Number: 4,528,405

[45] Date of Patent: Jul. 9, 1985

[54] ALDOL CONDENSATION OF ENOLIZABLE ALDEHYDES USING A METAL CARBOXYLATE CATALYST

[75] Inventor: Anthony J. Papa, St. Albans, W. Va.

[73] Assignee: Union Carbide Corporation, Danbury, Conn.

[21] Appl. No.: 567,423

[22] Filed: Dec. 30, 1983

[51] Int. Cl.³ .............................................. C07C 45/45
[52] U.S. Cl. ................................. 568/463; 568/459; 568/464
[58] Field of Search ................ 568/459, 462, 463, 464

[56] References Cited

U.S. PATENT DOCUMENTS

| 2,684,385 | 7/1954 | Bibbauer et al. | 568/463 |
| 3,248,428 | 4/1966 | Porter et al. | 568/463 |
| 3,968,135 | 7/1976 | Steele et al. | 260/438.5 R |
| 4,032,578 | 6/1977 | Savini | 568/459 |
| 4,169,110 | 9/1979 | Holavka et al. | 260/601 R |
| 4,210,767 | 7/1980 | Yoshida et al. | 568/345 |
| 4,270,006 | 5/1981 | Heilen et al. | 568/463 |
| 4,316,990 | 2/1982 | Morris | 568/459 |
| 4,328,379 | 5/1982 | Devon | 568/902 |

FOREIGN PATENT DOCUMENTS

| 101386 | 9/1978 | Japan | 568/459 |
| 1462328 | 1/1977 | United Kingdom | 568/878 |
| 791731 | 12/1980 | U.S.S.R. | 568/463 |

OTHER PUBLICATIONS

Irie et al., "Bull. Chem. Soc.", Japan, vol. 54, pp. 1195 to 1198, (1981); and vol. 53, pp. 1366 to 1371, (1980).
Irie et al., "Chem. Letters", pp. 539 to 540, (1978).
W. A. Benjamin, Menlo Park, Calif., "Modern Synthetic Reactions", 2nd Ed., Chapter 10, pp. 629–646, The Aldol Condensation and Related Reactions, (1972).
Walther et al., "Z. Anorg. Allg. Chem.", 440, pp. 22–30, (1978).
Iwata et al., "Bull. Chem. Soc.", Japan 49, (5), pp. 1369 to 1374, (1976).
Iwata et al., "Chem. Letters", pp. 959–960, (1974).

Primary Examiner—Werren B. Lone
Attorney, Agent, or Firm—Reynold J. Finnegan

[57] ABSTRACT

A process is disclosed for the aldol condensation of enolizable aldehydes to alpha, beta-unsaturated aldehydes, at high selectivities, employing a metal carboxylate catalyst.

8 Claims, No Drawings

ALDOL CONDENSATION OF ENOLIZABLE ALDEHYDES USING A METAL CARBOXYLATE CATALYST

BACKGROUND OF THE INVENTION

1. Field of the Invention

This invention relates to a process for the aldol condensation of alpha, beta-saturated aliphatic aldehydes and more particularly, to the use of certain metal carboxylates to catalyze the aldol condensation of such aldehydes.

2. Description of the Prior Art

The general commercial process for producing the alpha, beta-unsaturated aldehyde 2-ethyl-2-hexenal (known also as ethylpropylacrolein, or "EPA") by the self-condensation of n-butyraldehyde comprises a two-phase liquid reaction system in which the aldehyde is one phase and the other phase is an aqueous sodium hydroxide catalyst solution. Such caustic-catalyzed condensations are characterized by extremely high reaction rates of aldolization but yet require heating to high temperatures to cause dehydration of the intermediate aldol to the desired alpha, beta-unsaturated aldehyde. Thus, in the process, the condensation reaction cannot be terminated selectively and condensation continues, thereby producing high boiling by-products. For example, the desired product, EPA, condenses with n-butyraldehyde reactant to give the so-called Tishchenko trimers of n-butyraldehyde, including 2-ethyl-1,3-hexanediol monobutyrate and its various transesterification isomers. Thus, EPA selectivities are lower than desired with such a process.

Acids are also known to catalyze aldol condensation reactions. In contrast to base-catalysts, however, acids cause rapid dehydration of the aldol; thus, the final product compositions from condensations catalyzed by acids and bases can vary widely. A summary of some aqueous caustic and acidic catalyst systems for aldol condensations can be found in "Modern Synthetic Reactions" 2nd Ed., W. A. Benjamin, Menlo Park, Calif. (1972). On a commercial scale, aqueous sodium hydroxide solution is employed almost exclusively.

Various Group VIII metal catalyzed homogeneous liquid phase processes are known for the aldol condensation of aldehydes; however, these procedures are deficient in one or more aspects such as low reaction rates, use of non-enolizable (e.g. aromatic) aldehydes, need for an exotic solvent, or use of air-sensitive metal catalysts (e.g. nickel (O) derivatives). For example, Iwata et al. (*Bull. Chem. Soc. Japan* 49 1369, 1976; and *Chem. Letters* 959, 1974) disclose the aldol condensation of aldehydes with ketones promoted by the copper(II)ion. The yield of condensation product was increased by the addition of the zinc(II)ion. Irie et al. (*Bull. Chem. Soc. Japan* 54 1195, 1981; Irie and Watanabe *Bull. Chem. Soc. Japan* 53 1366, 1980; and *Chem. Letters* 539, 1978) report on the condensation of aldehydes with ketones employing catalyst complexes of 2,2'-bipyridine and first-row transition metal acetates, particularly Co(II), Ni(II), Cu(II) and Zn(II). One specific reaction studied is the condensation of benzaldehyde with acetophenone in a DMF solvent containing a cobalt acetate/2,2'-bipyridine catalyst complex. Walther et al. (*Z. Anorg. Allg. Chem.* 440 22, 1978) disclose the catalytic dimerization of propionaldehyde by mixed ligand-nickel(O) complexes, specifically the complex (2,2'-bipyridine) nickel(O) (triphenylphosphine)$_2$. U.S. Pat. No. 4,169,110 discloses the use of Group VIII metal salts (e.g., iridium chloride and rhodium chloride) as catalysts in the condensation of aldehydes to produce acetals and alpha, beta-unsaturated aldehydes. U.S. Pat. No. 4,210,767 discloses the use of zinc acetate as a catalyst for an aldol condensation. Russian Pat. No. 791,731 discloses the use of a cobalt naphthenate catalyst to produce 2-ethylhexenal by the condensation of n-butyraldehyde.

SUMMARY OF THE INVENTION

It has now been found that certain metal carboxylates catalyze the aldol self-condensation of enolizable aldehydes to alpha, beta-unsaturated aldehydes at high selectivity. The metals are selected from the group consisting of copper, magnesium, zinc, and the transition elements of Groups IV, V, VI, VII and VIII.

DESCRIPTION OF THE PREFERRED EMBODIMENTS

The process of the present invention generally comprises the liquid phase, aldol self-condensation of enolizable aldehydes to alpha, beta-unsaturated aldehydes employing certain metal carboxylates as homogeneous catalysts; specifically the carboxylates of the transition metals of Groups IV, V, VI, VII and VIII of the Mendeleev Periodic table and copper, magnesium and zinc. Generally, these metal carboxylates may be used to produce alpha, beta-unsaturated aldehydes from any enolizable aldehyde by an aldol self-condensation. The terminology "enolizable aldehyde" is used in its ordinary sense and is understood by those skilled in the art to include any saturated aliphatic aldehyde capable of conversion to alpha, beta-unsaturated aldehydes by aldol self-condensation. Examples of suitable enolizable aldehydes which may be subject to aldol self-condensation by the process of the present invention are butyraldehyde, propionaldehyde, valeraldehyde, hexaldehyde, and acetaldehyde. The resulting alpha, beta-unsaturated aldehydes are useful as intermediates in the production of acids, alcohols and plasticizers for certain compounds. The process of the present invention is especially useful for the aldol condensation of butyraldehyde and propionaldehyde to EPA and 2-methyl-2-penteneal, respectively.

The aldol condensation process of the present invention offers significant advantages over prior art processes. First, unlike certain other metal catalyst systems, the present invention works well with enolizable aldehydes. Second, the condensation reaction proceeds quite rapidly in the process of the present invention, as compared with certain other acid catalysts. Thirdly, the present process can be conveniently directed to favor production of certain condensation products. Specifically, by suitable control of the reaction conditions, the production of either alpha, beta-unsaturated aldehydes or Tishchenko Trimers can be favored. These and other advantages will be apparent to those skilled in the art from the following description.

The process of the present invention may be conducted batchwise, but a continuous operation is preferred for commercial production. In either mode, conventional equipment may be employed. In a typical laboratory batchwise operation, an aldehyde is added slowly (e.g., dropwise) to a solution of the metal carboxylate catalyst dissolved in a suitable solvent at a convenient temperature (e.g., about 70°–100° C.). The preferred solvents are higher boiling than the product to simplify product isolation. An exothermic reaction takes place during aldehyde addition. The reaction temperature is then maintained by any suitable means for about 30 minutes to several hours. As the condensation reaction proceeds, water is formed which generally produces an azeotrope with the starting aldehyde. The water layer of the azeotrope may be removed while the starting aldehyde is returned to the reaction vessel. If the water is not removed, it separates as a second phase in the reaction vessel. In any event, the product aldehyde may be recovered by known techniques. One possible continuous process may be conducted by continuously feeding starting aldehyde and catalyst solution to a reactor. The liquid product (containing starting aldehyde, aldehyde condensation product, water, solvent and catalyst) from the reactor may be stripped (e.g., in a vaporizer) of product, unreacted aldehyde and water as an overhead stream and the stripper underflow will contain recycle solvent and catalyst. The stripper overhead stream may be distilled to remove lower boiling unreacted aldehyde and water, the product aldehyde may be recovered by any suitable means and unreacted aldehyde may be recycled to the reactor. Those skilled in the art should be able to select appropriate process equipment for either batchwise or continuous operation.

Although the use of a solvent is not necessary in the process of the invention since the metal carboxylate catalyst is normally soluble in the starting aldehyde, it is preferred to employ a solvent to improve the efficiency of the reaction. Preferred solvents include the Tishchenko Trimer of n-butyraldehyde and other similar materials, such as the Tishchenko Trimer of isobutyraldehyde available from Eastman Chemical under its tradename "Texanol."

In the course of most aldol condensations, including that of the present invention, several by-products are formed. The "Tishchenko Trimers" are frequently-occurring by-products and are generally undesirable in the process of the invention inasmuch as their formation reduces the efficiency of alpha, beta-unsaturated aldehyde production. In addition, the possibility of Tishchenko Trimer formation and build-up in a homogeneous system, as in the process of the present invention, may be enhanced by liquid recycle streams. These trimers are formed when the aldol intermediate product reacts further with the starting aldehyde to form the final Tishchenko Trimers that are composed of three units of the starting material.

Control of the production of these Tishchenko Trimers is therefore desirable and can be accomplished by careful regulation of the reaction conditions. For example, some of the catalysts useful in the present invention (such as zirconium carboxylates and cobalt naphthenate) may favor the production of these trimers under certain reaction conditions, while others (such as chromium(III) carboxylates and nickel(II) carboxylates) are both excellent catalysts for aldehyde formation and tend to suppress Tishchenko Trimer formation. The presence of oxygen or water tends to direct the process towards the production of such trimers and should therefore be avoided. Because water is produced in the course of the reaction, it preferably should be removed as it is produced to minimize formation of such trimers. It has also been observed that when certain catalysts are dissolved in a solvent before addition to the reaction mixture, formation of these trimers may be increased.

Additionally, certain solvents (such as hexamethylphosphoramide or HMPA) may encourage Tishchenko Trimer formation and should be avoided. In summary, by suitable selection of the catalyst and by suitable control of the reaction conditions, formation of these trimers may be minimized. On the other hand, should one desire to produce predominantly these trimers (since they do have value and utility and their efficient production would be useful), conditions may be selected to accomplish such a result.

Accordingly, one embodiment of the present invention is a process for producing these trimers selectively. More specifically, the formation of Tishchenko Trimers from enolizable aldehydes is favored by certain metal carboxylates (i.e., certain manganese, copper, cobalt, iron and zirconium carboxylates), by the presence of water and oxygen during the aldol condensation reaction, by low pH and by the presence of certain solvents. The particular conditions tending to increase Tishchenko Trimer formation are illustrated in the Examples hereinbelow.

The carboxylates that may be used as the catalyst anion in the present invention are those which provide a catalyst soluble in the aldehyde to be condensed. A broad range of such compounds exist. Suitable carboxylates may be represented by the general formula:

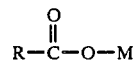

where M represents the catalyst metal and R represents a $C_1$–$C_{31}$ hydrocarbon group, which may be branched or un-branched, unsaturated or saturated or unsubstituted or substituted. In addition, the hydrocarbon group R may include a saturated or aromatic ring system, such as a cyclohexyl, naphthyl or phenyl group. Examples of suitable carboxylates include propionates, butyrates, 2-ethyl hexanoates, benzoates, etc. and also include those derived from fatty acids such as stearic acid, lauric acid and the like. It is preferred that the hydrocarbon group R be a $C_3$–$C_8$ hydrocarbon with 2-ethyl hexanoates being especially preferred. Other useful carboxylates are naphthenic acid metal salts.

The solubility of the metal carboxylate in the starting aldehyde may be improved, if necessary, by forming a complex thereof with an amine or phosphine ligand. Examples of suitable amines include aromatic amines such as 2,2'-bipyridine, pyridine, 4,4'-dimethyl-2,2'-bipyridine, 4-cyanopyridine, 4,4'-dimethylaminopyridine. Examples of suitable phosphines include triphenylphosphine, bis(1,2-diphenylphosphine)ethane, tri-n-butyl phosphine, trihexylphosphine. However, the use of such catalyst complexes may have an adverse effect on the selectivity, rate and productivity of the reaction. Therefore, care should be exercised in selecting a suitable ligand. For example, in the aldol self-condensation of n-butyraldehyde to EPA employing a nickel 2-ethylhexanoate catalyst, the addition of a pyridine or triphenylphosphine ligand can improve reaction selectivity with essentially no change in conversion or rate, depending upon the molar ratio of ligand to metal, (e.g., higher pyridine to nickel mole ratios increase heavies formation-a result also noticed when a ligand such as 2,2'-bipyridine is complexed with nickel 2-ethyl-hexanoate). Such catalyst complexes may be prepared by methods known to those skilled in the art.

The metal acetates are not generally soluble in either the starting aldehyde or in the resulting aldehyde condensation product. However, acetates such as nickel acetate may be either complexed with a suitable ligand and/or employed with a strong organic solvent such as dimethyl sulfoxide (DMSO) to improve selectivity to the desired aldehyde condensation product (see Examples 21–30 hereinbelow).

The catalyst metal may be a transition metal of Groups IV, V, VI, VII or VIII or copper, zinc or magnesium. Examples of suitable metals include chromium, iron, manganese, copper, nickel, zinc, zirconium, cobalt, magnesium, titanium, vanadium, hafnium, and the like.

Of all the metal carboxylates, the presently preferred one is chromium (III) 2-ethylhexanoate.

An advantage of the present invention is that it employs catalysts which are readily available from commercial suppliers and are not unusually expensive. In addition, these catalysts may be prepared by known methods, such as those described in U.S. Pat. Nos. 4,328,379 and 3,968,135, the disclosures of which are incorporated herein by reference.

The amount of catalyst used in the process is important and is generally characterized as a catalytic amount. Acceptable reaction rates may be obtained at catalyst concentrations as low as about 0.05 mole % and as high as about 2.0 mole %, based on the moles of starting aldehyde. It is preferred to use a catalyst concentration of about 0.3 to 1.0 mole %, based on the moles of starting aldehyde. The optimum catalyst concentration may vary with different aldehydes and different catalysts. For example, when using a chromium (III) 2-ethylhexanoate catalyst to condense n-butyraldehyde, optimal reaction rates are achieved when the catalyst is present in amounts of at least about 0.64 mole %.

The condensation reaction of the present invention proceeds quite rapidly and is strongly exothermic. For this reason, the reaction mixture is preferably cooled during the reaction to avoid over-heating. Excessive heat accumulation can cause loss of reactants and products due to evaporation or boiling and may result in dangerously high pressures. A variety of conventional cooling methods may be used for this purpose. The condensation reaction is not known to be otherwise adversely affected by temperature. The rapidity of this exothermic reaction, as has been noted, is an important advantage of the present process. The reaction is allowed to proceed, with cooling, for a period of time and at a temperature sufficient to obtain good yields of product. For example, using 0.64 mole %, based on the moles of n-butyraldehyde, of chromium(III) 2-ethylhexanoate as a catalyst to condense n-butyraldehyde, the reaction proceeds to 50% completion in about 4 minutes.

The following examples are provided to further illustrate the present invention and enable those skilled in the art to practice the invention. All of the examples describe work which was actually conducted. The examples are meant to be illustrative only and it is not intended to limit the invention thereby. Rather, it is intended that the invention be limited only by the scope of the claims appended hereto.

In the examples, percent product conversion was determined as [(equivalents of unreacted aldehyde in the product) less (equivalents of aldehyde reacted to form product)] × 100. The rate of production in the reaction (moles of aldehyde per liter-hour) was determined by dividing the number of moles of product per hour by the total reaction volume. Percent efficiency was determined as $$\frac{\text{aldehyde equivalents used to form alpha, beta-unsaturated aldehyde in product}}{\text{(equivalents of aldehyde in product mixture) less (equivalents of unreacted aldehyde in product)}} \times 100;$$

percent yield was determined as [(aldehyde equivalents used to form product)/(equivalents of aldehyde in product mixture)] × 100; a molecular weight of 126 was assumed for the lights (i.e., the beta, gamma-isomer of EPA); and a molecular weight of 180 was assumed for the unknown heavy species (i.e., same molecular weight as trimer or 3×butraldehyde less 2×water=180).

EXAMPLES 1–3

Various amounts of fresh chromium 2-ethylhexanoate catalyst and n-butyraldehyde Tishchenko trimer solvent were separately introduced into a 125 ml round-bottom, glass reaction vessel provided with a stirrer and with a conventional column and head designed for removal of water as formed. The resulting mixture was heated in the vessel to about 100° C. with stirring until a homogeneous mixture resulted. 0.25 mole of butyraldehyde was then added dropwise, with stirring, resulting in an exotherm. The temperature was controlled to 100°–120° C. for 2 hours and the contents of the reaction vessel (i.e., the organic phase) were periodically sampled. Water was continuously removed from the vessel during the reaction. The organic phase was analyzed by gas chromatography. A Hewlett Packard series 5880A gas chromatograph equipped with a 15 foot ⅛ inch diameter stainless steel column packed with 10 percent QF-1 on Chromosorb W H.P. was programmed up to 200° C. with a thermal conductivity detector. The results are shown in Table I below.

As is apparent from Table I, the butyraldehyde aldol condensation reaction proceeds more rapidly, and with fewer heavy and light molecular weight by-products, when the catalyst concentration is increased.

TABLE I

| Example | Reaction Time (Minutes) | Reaction Rate (Mole/L-hr) | Butyraldehyde Conversion (%) | Heavies[d] Produced (%) | Lights[d] Produced (%) |
| --- | --- | --- | --- | --- | --- |
| Example 1[a] | 15 | 10.6 | 22 | 4.0 | 1.1 |
|  | 30 | 5.6 | 23 | 1.2 | 0.8 |
|  | 45 | 4.1 | 26 | 1.4 | 0.8 |
|  | 60 | 3.8 | 32 | 1.6 | 1.3 |
|  | 120 | 3.0 | 50 | 1.8 | 1.3 |
| Example 2[b] | 60 | 6.5 | 86 | 2.5 | 0.5 |
|  | 120 | 3.8 | 86 | 1.1. | 1.0 |
| Example 3[c] | 15 | 12.9 | 70 | 0 | 0.1 |
|  | 30 | 7.5 | 82 | 0 | 0.2 |
|  | 45 | 5.4 | 86 | 0 | 0.2 |
|  | 60 | 3.8 | 85 | 0 | 0.3 |
|  | 90 | 2.6 | 86 | 0 | 0 |
|  | 120 | 2.0 | 86 | 0 | 0.2 |

[a] 0.8 millimoles (0.11 mole %) of catalyst in 4.6 grams of solvent
[b] 1.6 millimoles (0.64 mole %) of catalyst in 9.2 grams of solvent
[c] 3.61 millimoles (1.44 mole %) of catalyst in 30 grams of solvent
[d] Amounts of heavies and lights, respectively, based on all products, as gas chromatograph area percents

EXAMPLES 4-9

In addition to the chromium ethylhexanoate catalyst used in Examples 1-3, other metal carboxylates may be used in the process of present invention. Examples 4 through 9 illustrate the use of cobalt (II), iron (III), zinc, zirconium, nickel (II) and chromium (III) ethylhexanoate catalysts. The same apparatus employed in Examples 1-3 was used. The various metal 2-ethylhexanoate catalysts were added to 0.25 mole of butyraldehyde in the absence of solvent. In example 7, 4.11 mmoles of catalyst were used. In Examples 4-6, 8 and 9, 7.23 mmoles were used. The catalysts dissolved on warming. The mixtures were stirred and heated for one hour at 80°-120° C. with removal of water as formed. The results are shown in Table II. A comparison between these examples shows that, while all of the catalyst compounds give good results, chromium (III) ethylhexanoate is preferred because of its high conversion rate and relatively low production of by-products.

TABLE II

| Example/ catalyst Metal | Reaction Rate (Moles/ L-hr) | BuAl[a] Conversion (%) | EPA[b] Produced (M Moles) | T/N[c] | Heavies Produced (%) | Lights Produced (%) |
|---|---|---|---|---|---|---|
| 4/Co(II) | 4.8 | 88 | 52.9 | 661 | 8.9 | 9.0 |
| 5/Fe(III) | 5.0 | 92 | 69.1 | 668 | 38.0 | 11.9 |
| 6/Zn | 6.7 | 15 | 5.9 | 230 | 8.4 | 2.7 |
| 7/Zr | 9.8 | 90 | 57.5 | 2,383 | 42.0[d] | 4.2 |
| 8/Ni(II) | 4.7 | 86 | 101.6 | 649 | 5.2 | 1.0 |
| 9/Cr(III) | 15.3 | 94 | 111.6 | 3,020 | 7.4 | 1.5 |

[a] BuAl = butyraldehyde
[b] EPA = ethylpropylacrolein
[c] T/N = Turnover Number = moles of EPA produced per mole of catalyst
[d] of this amount, 34.3 percent is the Tishchenko trimer

EXAMPLES 10-14

Using the same apparatus and same general procedure as in Examples 1-3, 0.25 mole of buyraldehyde was added to various metal 2-ethylhexanoate catalysts dissolved in 30 grams of various solvents and allowed to react for one hour at 100°-120° C. with removal of water as formed. The results are shown in Table III below. In examples 10 and 11, 2.9 mole % of nickel catalyst was used. In examples 12, 13 and 14, 1.4 mole % of a chromium (III) catalyst was used. The use of a solvent increases the selectivity of the process toward the desired products, but decreases the total yield.

TABLE III

| Example | Reaction Rate (Moles/ L-hr) | Butyraldehyde Conversion % | EPA Produced (M Moles) | T/N | Heavies Produced (%) | Lights Produced (%) |
|---|---|---|---|---|---|---|
| 10 | 4.7 | 86 | 101.6 | 649 | 5.2 | 1.0 |
| 11 | 2.3 | 80 | 102.7 | 323 | 0.3 | 0.5 |
| 12 | 15.3 | 95 | 111.6 | 3,020 | 7.4 | 1.5 |
| 13 | 5.4 | 85 | 108.6 | 1,492 | 0.0 | 0.2 |
| 14 | 8.0 | 85 | 97.0 | 2,222 | 0.0 | 0.9 |

Note:
| Example | Catalyst Metal | Solvent |
|---|---|---|
| 10 | Ni (II) | none |
| 11 | Ni (II) | n-butyraldehyde Tishchenko trimer ("n-tt") |
| 12 | Cr (III) | none |
| 13 | Cr (III) | n-tt |
| 14 | Cr (III) | iso-butyraldehyde Tishchenko Trimer (Available from Eastman Chemical under the Tradename Texanol) |

EXAMPLES 15-20

Using the same apparatus and same general procedure as in Examples 1-3, a mixture of butyraldehyde and different metal stearate catalysts (in the absence of solvent) was heated to about 80° C. at which time refluxing commenced and essentially all the catalyst dissolved. The reaction was completed by heating the resulting mixture with stirring at 80°-120° C. for two hours with removal of water as formed. The results are shown in Table IV below.

TABLE IV

| Example/ Metal Stearate | Reaction Rate (Moles/L-hr) | BuAl Conv. (%) | EPA Produced (M Moles) | T/N | Tishchenko Trimer Produced (M Moles) | Heavies Produced (%) | Lights Produced (%) |
|---|---|---|---|---|---|---|---|
| 15/Ni(II) | 1.9 | 41 | 49.2 | 264 | no data | 4.3 | 0.5 |
| 16/Cr(III) | 4.2 | 92 | 110.8 | 835 | no data | 3.9 | 1.3 |
| 17/Co(II) | 4.0 | 87 | 102.1 | 558 | no data | 7.5 | 1.7 |
| 18/Cu(II) | 2.4 | 52 | 45.3 | 334 | 12.4 | 1.6 | 1.1 |
| 19/Mn(II) | 4.3 | 93 | 99.6 | 594 | 13.1 | 1.8 | 1.5 |
| 20/Mg | 3.9 | 85 | 95.9 | 543 | 9.4 | 1.6 | 0.1 |

Note:
For examples 15, 16 and 17, Tishchenko Trimer production is included in Heavies production.

EXAMPLES 21-30

In Example 23, using the same apparatus and general procedure as in Examples 1-3 above, 0.25 mole of butyraldehyde was added dropwise at about 70° C. to a solution of 7.23 millimoles of nickel acetate tetrahydrate complexed with 2,2' bipyridine dissolved in 20 grams of various solvents. A similar, uncomplexed catalyst was used in Examples 21, 22 and 24-30. The reaction conditions and results are set forth in Table V below.

TABLE V

| Example | Solvent | Reaction Conditions | EPA produced (m moles) | T/N |
|---|---|---|---|---|
| 21 | None | 2 hrs. at 75° C. | 5.1 | 1 |
| 22 | TMU[a] | 2 hrs. at 93° C. | No reaction | |
| 23 | TMU | 2 hrs. at 105°-125° C. | 115.7[h] | 16 |
| 24 | DMSO[b] | 1.5 hrs. at 113° C. | 94.5[g] | |
| 25 | DMF[c] | 2.0 hrs. at 97° C. | 21.7[j] | 3 |
| 26 | CH₃CN[d] | 2.0 hrs. at 75° C. | 0.7 | 0.1 |
| 27 | C₂H₅OH[d] | 2.0 hrs. at 75° C. | 0.9 | 0.1 |
| 28 | H₂O | 2.0 hrs. at 70°- | No detectable product | |
| 29 | tetramethylene sulfoxide | 2.0 hrs. at 100°-137° C. | 105.6[c] | 15 |

TABLE V-continued

| Example | Solvent | Reaction Conditions | EPA produced (m moles) | T/N |
|---|---|---|---|---|
| 30 | Sulfolane | 2.0 hrs. at 75°-95° C. | 37.4 | 5 |

[a]TMU = tetramethyl urea
[b]DMSO = dimethyl sulfoxide
[c]dimethyl formamide
[d]solid precipitated from solution on addition of the butyraldehyde
[e]Unknown lights = 3.4 millimoles and heavies = 1.1 millimoles
[f]Unknown heavies = 5.5 millimoles
[g]Unknown lights = 0.9 millimole and heavies = 1.1 millimoles
[h]Unknown heavies = 14.4 millimoles

EXAMPLES 31-42

Examples 1-3 were repeated using 7.23 millimoles of nickel 2-ethylhexanoate catalyst dissolved in 30 grams of various solvents. The reaction was conducted for two hours at about 100°-120° C. The solvents and results are shown in Table VI below.

TABLE VI

| Solvent | BuAl Conversion (%) | Heavies (%) | Lights (%) |
|---|---|---|---|
| n-BuAl Tishchenko Trimer (n-TT) | 80 | 0.3 | 0.5 |
| Octane | 68 | 0 | 1.1 |
| Ethanol | 33 | 0.2 | 0.5 |
| 2-Ethylhexanoic acid | 36 | 0.5 | 0 |
| Diglyme | 37 | 1.1 | 0 |
| DMF | 85 | 1.1 | 0.8 |
| n-Propanol | 47 | 1.0 | 6.2 |
| N,N—Dimethylacetamide | 85 | 1.8 | 0.6 |
| Tetramethylurea | 71 | 2.4 | 0.9 |
| 2-Ethyl-hexanol | 84 | 3.4 | 0.4 |
| Nonane | 83 | 3.9 | 0.3 |
| Ethyl propyl acrolein (EPA) | 68 | 4.4 | 1.5 |
| None | 86 | 5.2 | 1.0 |
| Acetic acid | 31 | 5.1 | 6.8 |
| Dimethylsulfoxide | 83 | 5.6 | 4.5 |
| Toluene | 83 | 6.1 | 0 |
| Water[a] | 32 | 6.6 | 2.0 |
| 2-ethyl-1-hexanediol | 89 | 8.3 | 5.2 |
| 3-GH Plasticizer | 31 | 8.9 | — |
| n-Decanol | 84 | 11.2 | 0.7 |
| Hexamethylphosphoramide | 74 | 16.9 | 1.7 |
| Pyridine oxide | 90 | 19.0 | 15.3 |
| Triphenylphosphine oxide | 83 | 24.3 | 1.8 |
| Butyl CARBITOL acetate | 17 | — | — |

[a]only 20 grams of water employed (using only 2 grams gave similar results)

EXAMPLES 43-48

Examples 43-48 show the effect of oxygen on the selectivity of butyraldehyde condensation. The presence of oxygen gives high butyraldehyde conversions, but it directs the reaction toward the formation of the Tishchenko trimer. Using the same apparatus and general procedures as in Examples 1-3 above, and in the absence of solvent, a mixture of 0.25 mole of butyraldehyde and 7.23 millimoles of various anhydrous solid catalysts (except that the iron(II) acetate catalyst did not dissolve in the butyraldehyde) was heated at 80°-90° C. for the times indicated in Table VII below while passing a small stream of either air or nitrogen under the liquid surface by means of a sparging tube. The results are also shown in Table VII.

TABLE VII

| Example/Catalyst | Atmosphere | Reaction Time (hr) | BuAl Conv. (%) | EPA Yield (%) | Tishchenko Trimer Yield (%) |
|---|---|---|---|---|---|
| 43/None | Air | 1 | 39[a] | 3.3 | 18.6 |
| 44/Fe(II) Acetate | Nitrogen | 2 | 12 | 5.9 | 5.4 |
| 45/Fe(II) Acetate | Nitrogen | 4 | 17 | 10.5 | 3.9 |
| 46/Fe(II) Acetate | Air | 1 | 100 | 52.5 | 38.0 |
| 47/Ni(II) 2-Ethylhexanoate | Nitrogen | 2 | 86 | 79.1 | 5.2 |
| 48/Ni(II) 2-Ethylhexanoate | Air | 2 | 70[b] | 44.1 | 17.7 |

[a]Obtained some butyric acid as well (yield, 4.4%).
[b]Also obtained some butyric acid (yield, 1.6%).

EXAMPLES 49-52

Examples 49 through 52 demonstrate the effect of both oxygen and solvent on Tishchenko trimer yield. The general procedure of Examples 43-48 was repeated except that a cobalt naphthenate catalyst (0.367 mole of Co metal, obtained from a 6% Co commercial sample) in 0.25 mole of butyraldehyde, containing either a nitrogen or air sparge, was heated for one or two hours at 120° C., using 20 grams of hexamethylphosphoramide (HMPA) solvent in some cases. The specific reaction conditions and results are shown in Table VIII below. The data set forth in Table VIII shows that the trimer can be made the major product. Oxygen and hexamethylphosphoramide solvent are shown to contribute equally to increased trimer production.

TABLE VIII

| Example | Atmosphere | Solvent | Butyraldehyde Conversion (%) | EPA Yield, (%) | Tishchenko Trimer Yield, (%) |
|---|---|---|---|---|---|
| 49 | Air | HMPA[a] | 98 | 36.1 | 53.3 |
| 50 | Nitrogen | HMPA[a] | 94 | 62.1 | 28.3 |
| 51 | Air | None[b] | 87[c] | 46.9 | 21.4 |
| 52 | Nitrogen | None[b] | 92 | 77.0 | 7.6 |

[a]Reaction time = 2 hrs.
[b]Reaction time = 1 hr.
[c]Reaction also gave butyric acid (yield 4.6%).

EXAMPLES 53-56

Using the same apparatus and general procedure as in Examples 1-3 above, a mixture of 0.50 mole of various aldehydes and 7.23 millimoles of chromium (III) 2-ethylhexanoate catalyst was heated for various times at reflux, in the absence of a solvent, with removal of water as formed. When acetaldehyde was used in Example 53, relatively poor results were obtained. Twenty-five percent of the product was crotonaldehyde and the remainder was a mixture of unknown products. The crude product from each of the examples was analyzed. The specific reaction conditions and results are shown in Table IX below.

TABLE IX

| Example | Aldehyde Conversion (%) | Reaction Rate (Moles/L-hr) | T/N | Lights (M Moles) | Heavies (M Moles) | Reaction Time (Min) |
|---|---|---|---|---|---|---|
| 53 | 67 | — | — | — | — | 180 |
| 54 | 90 | 6.3 | 32 | 8.3 | 60.4 | 60 |
| 55 | 86 | 16.0 | 32 | 0 | 3.4 | 30 |
| 55 | 74 | 18.0 | 24 | 0 | 9.7 | 15 |

Note:

TABLE IX-continued

| Example | Aldehyde | Product (M Moles) |
|---------|----------|-------------------|
| 53 | acetaldehyde | crotonaldehyde |
| 54 | propionaldehyde | 2-methyl-2-pentenal (228.5) |
| 55 | valeraldehyde | 2-propyl-2-heptenal (230.6) |
| 56 | hexaldehyde | 2-butyl-2-octenal (271.1) |

What is claimed is:

1. In a process for the production of alpha, beta-unsaturated aldehydes by the aldol condensation of enolizable aldehydes in the presence of a catalyst, and wherein water is removed as formed during the reaction, the improvement comprising using as said catalyst a metal carboxylate selected from the group consisting of chromium (III) 2-ethylhexanoate and nickel (II) 2-ethylhexanoate.

2. The process of claim 1 wherein said catalyst is present in a concentration of at least 0.05 mole percent, based on the moles of enolizable aldehyde.

3. The process of claim 2 wherein said catalyst is present in a concentration of between 0.3 and 1.0 mole percent.

4. The process of claim 3 wherein said enolizable aldehyde is selected from the group consisting of butyraldehyde, propionaldehyde, hexaldehyde.

5. The process of claim 1 wherein said enolizable aldehyde is butyraldehyde.

6. The process of claim 1 wherein said catalyst is complexed with an organic amine or a phosphine ligand.

7. The process of claim 1 wherein said catalyst is soluble in said enolizable aldehyde.

8. The process of claim 1 wherein said catalyst is chromium (III) 2-ethylhexanoate.

* * * * *